United States Patent [19]

Nakamoto

[11] Patent Number: 4,640,274

[45] Date of Patent: Feb. 3, 1987

[54] SURGICAL NEEDLE EXTRACTOR HAVING A DISPOSABLE CHUCK, A CHUCK AND A HANDLE

[75] Inventor: Takayuki Nakamoto, Tokyo, Japan

[73] Assignee: Iwata Electric Works Co., Ltd., Tokyo, Japan

[21] Appl. No.: 487,290

[22] Filed: Apr. 21, 1983

[30] Foreign Application Priority Data

Dec. 2, 1982 [JP] Japan .................................. 57-212547

[51] Int. Cl.$^4$ .............................................. A61B 17/10
[52] U.S. Cl. ................................. 128/321; 128/303 R; 81/421; 254/28
[58] Field of Search .................... 128/303 R, 321, 325; 254/28, 27; 81/421-423, 300, 342, 349; 30/260; 206/438, 439, 363, 339

[56] References Cited

U.S. PATENT DOCUMENTS

| | | | |
|---|---|---|---|
| 1,108,737 | 8/1914 | Gajdos ................................. | 128/340 |
| 1,359,164 | 11/1920 | Lo Giudice et al. ................ | 128/321 |
| 1,783,583 | 12/1930 | Ralston ................................ | 30/260 |
| 2,109,147 | 2/1938 | Grosso ................................ | 128/321 |
| 2,113,246 | 4/1938 | Wappler .............................. | 128/321 |
| 2,202,984 | 6/1940 | Drypolcher ......................... | 254/28 |
| 4,152,920 | 5/1979 | Green .................................. | 128/325 |
| 4,211,325 | 7/1980 | Wright ................................ | 206/438 |
| 4,293,119 | 10/1981 | Diederichs .......................... | 254/28 |
| 4,412,617 | 11/1983 | Cerwin ................................ | 206/339 |

FOREIGN PATENT DOCUMENTS

| | | | |
|---|---|---|---|
| 59778 | 9/1982 | European Pat. Off. ............. | 254/28 |
| 214727 | 2/1924 | Fed. Rep. of Germany ...... | 128/321 |
| 401732 | 9/1909 | France ................................ | 128/321 |

Primary Examiner—Michael H. Thaler
Attorney, Agent, or Firm—Sandler & Greenblum

[57] ABSTRACT

A surgical needle extractor is provided which has a chuck including a penetration portion for penetrating between the claws of a surgical needle. The chuck also has an actuated piece pivotable with respect to the penetration portion of the chuck. The extractor includes a handle to which the chuck is releasably attached. The handle includes pivoting means for pivoting the actuated piece with respect to the penetration portion such that when the penetration portion is inserted between the needle claws, the penetration portion and the actuated piece cooperate to remove the needle. Only the chuck touches the patient's skin, and only the handle is touched by the operator. Accordingly, the handle need not be sterilized each time before use and the chuck is disposable. The actuating rod of the handle is adapted to be hand-operated. The extractor can further include means for releasing the chuck from the handle when a new chuck is desired to be attached to the handle. Both the chuck and the handle can be formed as unitary members.

35 Claims, 18 Drawing Figures

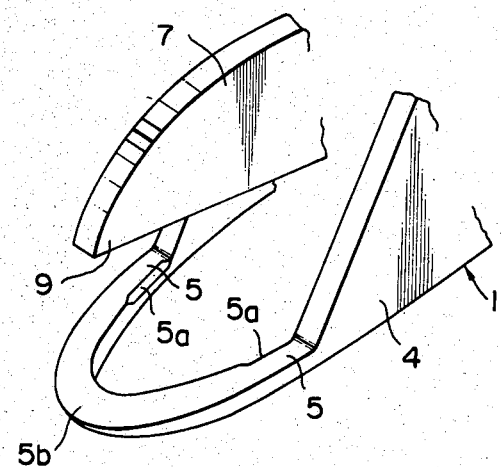
FIG. 9
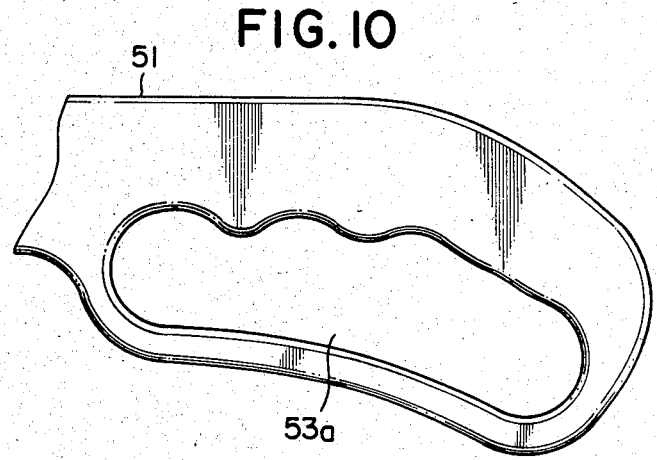
FIG. 10
FIG. 11
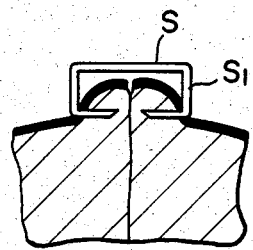
FIG. 12
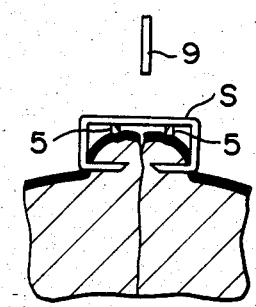

SURGICAL NEEDLE EXTRACTOR HAVING A DISPOSABLE CHUCK, A CHUCK AND A HANDLE

TECHNICAL FIELD OF THE INVENTION

The present invention relates to surgical needle extractors, and more particularly, to apparatus for extracting metallic surgical needles used for closing wounds after surgery.

BACKGROUND

Conventional surgical needle extractors are formed as unitary structures, and are generally made of metal. They are usually designed to be used once and then discarded because the cost of sterilization and storage for re-use exceeds the cost of the extractor itself. Accordingly, inefficient use is made of the material forming the extractor.

A conventional unitary needle extractor is shown in FIG. 18. Both the handle and the end element which touches the patient and removes the needle are formed as a single unit. Such an extractor is difficult to grasp and its handling is inconvenient, thus preventing smooth extraction of needles and increasing the time required for extraction. This is disadvantageous because it prolongs pain for the patient.

BRIEF SUMMARY OF THE INVENTION

Accordingly, in view of the above-stated deficiencies in the prior art, the present invention provides the following advantages.

Only the chuck need be disposable because only the chuck contacts the skin of the patient, and only the handle is touched by the operator. Thus, the chuck is releasably attached to the handle and can be released therefrom and exchanged for a new chuck after being used. The handle, therefore, need not be sterilized and can be re-used. Thus, sterilization and storage costs are eliminated, and personnel costs are reduced, producing an economical extractor.

Upon further study of the specification and dependent claims, further objects, features, and advantages of the present invention will become more fully apparent to those skilled in the art to which the invention pertains.

Briefly, the above and other objects, features, and advantages of the present invention are attained in one aspect thereof by providing a surgical needle extractor having a chuck including a penetration portion having means for penetrating between the claws of a surgical needle and an actuated piece which is pivotable with respect to the penetration portion of the chuck. The extractor also has a handle to which the chuck is releasably attached. The handle includes pivoting means for pivoting the actuated piece with respect to the penetration portion of the chuck such that when the penetration portion is inserted between the claws of the surgical needle, the penetration portion and the actuated piece cooperate to remove the needle. The extractor can also include means for releasing the chuck from the handle.

The above and other objects, features, and advantages of the present invention are obtained in another aspect thereof by providing a chuck for a surgical needle extractor, where the chuck has first and second members attached to one another, where one end of each of the first and second members include a penetration portion for penetrating between the claws of a surgical needle, and the chuck further includes an actuated piece which is disposed between and pivotably attached to the first and second members.

The above and other objects, features, and advantages of the present invention are obtained in yet another aspect thereof by providing a handle for a surgical needle extractor chuck, where the chuck is of a type having a penetration portion including means for penetrating between the claws of a surgical needle and an actuated piece pivotable with respect to the penetration portion, where the handle includes means for releasably attaching the chuck to the handle and also includes pivoting means for pivoting the actuated piece with respect to the penetration portion, such that when the penetration portion is inserted between the claws, the penetration portion and the actuated piece cooperate to remove the needle.

The above and other objects, features, and advantages of the present invention are obtained in still another aspect thereof by providing a container for a surgical needle extractor chuck where the chuck is of a type having a penetration portion including means for penetrating between the claws of a surgical needle, an actuated piece pivotable with respect to the penetration portion and an insert portion adapted to be releasably attached to a handle. The container includes a housing having an open area in which the chuck can be at least partially disposed. The container also includes a cover disposed over the housing open area for sealing the open area. The container also includes a support member disposed in the housing open area, the support member including means for releasably securing the chuck to the support member such that the insert portion of the chuck projects out of the support member, whereby when the cover is removed from the housing, the chuck can be attached to the handle without direct handling of the chuck.

The above and other objects, features and advantages of the present invention are obtained in yet another aspect thereof by providing a method of attaching a sterilized needle extractor chuck to a handle, wherein the chuck has a penetration portion including means for penetrating between the claws of a surgical needle, and an insert portion including means for inserting in a recess in the handle, and wherein the container has a housing having an open area in which the chuck is at least partially disposed, a cover disposed over the haousing area for sealing the open area, and a support member loosely disposed in the housing open area, the support member including means for releasably securing the chuck to the support member such that the insert portion of the chuck projects out of the support member, the method including removing the chuck from the housing, removing the support member and the chuck releasably secured to the support member from the housing open area, inserting the insert portion of the chuck into the recess in the handle, and releasing the chuck from the support member.

The above and other objects, features and advantages of the present invention are obtained and an additional aspect thereof by providing a method of attaching a sterilized surgical needle extractor to a handle, wherein the chuck includes a penetration portion having means for penetrating between the claws of a surgical needle, and an insert portion having means for inserting in a recess in the handle, and wherein the container includes a housing having an open area in which the chuck is at least partially disposed, a cover disposed over the housing open area for sealing the open area, the cover including an open area in which the insert portion can be disposed, and a support member secured in the housing open area, the support member including means for releasably securing the chuck to the support member such that the insert portion of the chuck projects out of the support member into the open area of the cover when the cover is over the housing, the method including removing the cover from the housing, inserting the insert portion of the chuck into the recess in the handle, and releasing the chuck from the support member.

A surgical needle extractor according to the present invention has a chuck which contacts the skin of a patient as the needle is extracted. The extractor also has a handle for holding the chuck. The chuck is releasably attached to the handle; it therefore can be ejected and exchanged for a new chuck. The handle has a recess within which the chuck is releasably attached; the chuck is tightly fitted within this recess. Surgical needles can be extracted using the chuck and handle which integrally cooperate with one another. However, only the handle is touched by the operator, and only the chuck touches the skin of a patient.

A chuck according to the present invention has an insert portion which is preferably fitted for releasable attachment within a first recess formed in a handle. The insert portion preferably has a substantially U-shaped section. This first recess is preferably formed at the front end of the handle. The chuck is preferably a unitary structure having first and second members. One end of each of the first and second members has a penetration portion for penetration between the claws of a surgical needle. The penetration portions are spaced apart from one another a predetermined distance, the spacing distance being smaller than the distance between the claws of a conventional surgical needle. The upper surfaces of the penetration portions are adapted as needle-holding surfaces, and the undersurfaces of the penetration portions are adapted as surfaces which are brought into contact with the skin of a patient. An actuated piece is pivotably attached between the first and second members. The actuated piece has a needle-pushing portion which can be pivoted such that it is inserted between the penetration portions in order to deform and remove a surgical needle. While the actuated piece is being pivoted, its rear side portion is pivoted away from the insert portion.

A handle according to the present invention has, preferably at its front end, a first recess into which the insert portion of the chuck is detachably fitted or inserted such that the chuck is releasably attached to the handle. The handle has, preferably at its rear side, a finger-holding surface. An actuating rod is pivotably attached to the handle, preferably near the first recess. One end of the actuating rod is disposed in a second recess in the handle; the second recess is in communication with the first recess. The actuating rod has a coupling portion, preferably at the front end of its front side, adapted to be releasably attached to the actuated piece of the chuck, preferably at the rear end of the rear side of the actuated piece, such that the actuated piece is free to pivot. The actuating rod includes a finger-holding surface, preferably at its rear side. A spring is disposed in the second recess of the handle for biasing the actuating rod, preferably against its rear side, such that the coupling portion of the actuating rod is in position for attachment with the actuated piece when the chuck is inserted into the first recess in the handle.

The coupling portion of the actuating rod is urged by the spring such that it is in position, preferably in the first recess in the handle in which the chuck is inserted, for releasable attachment to the actuated piece of the chuck. The coupling portion of the actuating rod preferably is attached to the end of the rear side of the actuated piece. Accordingly, chucks can be readily exchanged simply by extracting the used chuck from the first recess and inserting a new chuck therein.

Longitudinal grooves are formed in the first recess of the handle. Corresponding projections are formed on the insert portion of the chuck for engagement with these grooves during insertion of the chuck into the handle. Thus, erroneous or upside down insertion of the chuck into the handle is prevented.

The insert portion projections are preferably formed as longitudinal, belt-like projections and are dimensioned to tightly engage the first recess grooves. As a result, the insert portion is doubly prevented from moving within the first recess, and the chuck at the end of the handle is prevented from shaking while a needle is extracted.

The insert portion projections can have midpoint indentations for engagement with midpoint projections in the first recess grooves. By this provision, an operator can recognize when the insert portion is properly inserted in the first recess due to a sound produced when the insert portion projections move over the midpoint projections in the first recess grooves and immediately thereafter the midpoint projections abut against the midpoint indentations. This provides further insurance that the chuck will not come out of the needle.

The coupling portion of the actuating rod has a pivot pin. The rear end of the actuated piece has a groove in which the pivot pin can fit loosely to allow some play, such that the coupling portion and the actuated piece can cooperatively and reliably function.

The front end of the actuating rod is forked, and the pivot pin is disposed at this forked front end to provide a coupling portion for detachable connection with the above-mentioned groove in the rear end of the actuated piece. This coupling portion is dimensioned to have a width to fit in the insert portion of the chuck loosely to allow some play. The portion of the actuated piece containing the groove can fit between the forked front end of the coupling portion. The inner surfaces of the front end are beveled such that the coupling portion and the actuated piece can be smoothly and reliably attached to and released from each other.

The angle of inclination of the chuck surface which contacts the skin of a patient, the angle formed by the front and rear sides of the handle, the angle of inclination of the actuating rod relative to the front side of the handle, the angle formed by the front side and the finger-holding surface of the actuating rod, and the angle of inclination of the undersurface of the finger-holding surface of the actuating rod relative to the upper surface thereof are all set relative to each other with predetermined values such that the extractor according to the present invention can be freely handled as if it were an extension of the hand of an operator.

The first and second members of the chuck form a constricted guide portion for guiding the actuated piece such that the pivoting motion of the actuated piece is not hindered. As a result, the actuated piece can pivot in a predetermined manner without undesirable side movement, so that the needle can be smoothly extracted. In addition, because the pivoting motion of the actuating piece is not hindered, the actuated piece can be attached to the coupling portion of the actuating rod without being hindered.

The chuck has longitudinal elongated holes, preferably extending from the middle part of the chuck to the rear half of the first and second members of the chuck and to the front half of the insert portion of the chuck. As a result, the middle part of the chuck can be bent sufficiently such that the needle holding surfaces of the chuck can be smoothly expanded during the extraction. This results in smooth deformation of the surgical needle and effective extraction thereof.

The penetration portions of the chuck can be connected together by a penetration guiding collar, thereby enabling smooth penetration of the penetration portions below the surgical needle.

The upper surface of the finger-holding surface of the actuating rod is preferably shaped to have a concave section from a side view thereof. As a result, the inner surface of the thumb conforms to this concave surface and does not easily slip off so that the needle can be reliably and readily extracted. In addition, the upper surface of the fingerholding surface of the actuating rod is shaped to have a concave section from a front side view thereof. Accordingly, the thumb of the operator will not slip right or left, and the needle can be readily removed.

The finger-holding surface of the handle also has a concave portion which corresponds to the shape of the inner surfaces of the forefinger, middle finger, ring finger and little finger. Thus, the fingers of an operator will fit this surface readily to enable a firm grasp. The finger-holding surface of the handle can be annular such that the fingers of an operator can integrally cooperate with the surface to facilitate handling. Further, both the finger-holding surface of the holder and that of the actuating rod can be made annular to provide handling similar to that provided by scissors.

The handle may be formed of a pair of right and left components assembled into a unitary structure. These right and left components, along with a coupling shaft, the pivot shaft to which the actuating rod is pivotally attached to the handle, and the shafts on which the spring is secured, can all be formed as an integral structure, thus facilitating fabrication and assembly and reducing production costs.

Both the right and left portions of the upper surface of the front side of the holder can be beveled to form cut-surfaces such that the chuck can still be observed by the operator within a wide visual range in order to facilitate extraction of needles.

Means for releasing the chuck from the handle can also be provided. The means for releasing the chuck from the handle can constitute an actuating rod slidably attached to the handle whereby sliding the actuating rod with respect to the handle releases the chuck from the handle. The actuating rod includes a hole in which a pivot shaft is fitted connecting the actuating rod to the handle; this hole is a longitudinal elongated hole, allowing the actuating rod to slide with respect to the pivot shaft. The actuating rod which forms the releasing means can be the same as the actuating rod which forms the pivoting means for pivoting the actuated piece with respect to the penetration portion. Thus, the actuating rod for the releasing means can also be subject to the bias of the above-mentioned spring. In such case, a portion of the rear side surface of the actuating rod against which the spring abuts may be indented. An angled projecting portion is formed on the spring for engagement with this concave portion of the actuating rod. Thus, when the actuating rod is pivoted, the actuated piece likewise is pivoted and the chuck carries out a predetermined needle extraction operation. As the actuating rod is pivoted, ultimately the concave portion of the actuating rod will move beyond the projecting portion of the spring. At this time, the coupling portion at the front end of the actuating rod is capable of being freely advanced and retracted due to the ability of the actuating rod to slide with respect to its pivot shaft; the coupling portion can be advanced until it projects out of the first recess in the handle, and thus releases the chuck from the handle. Accordingly, the chuck can be released from the handle by a one-touch operation by pushing the actuating rod forwardly with the thumb of the operator while the hand of the operator grasps the handle. Thus, a disposable chuck can be readily separated from the handle by a one-hand operation without requiring touching of the chuck by the operator. In addition, the needle extraction and the chuck release operations can be performed by a single actuating rod.

The finger-holding surface of the actuating rod has an upper surface portion to which the thumb of the operator is applied when the actuating rod is pushed down toward the holder to pivot the actuated piece, and a rear surface porton to which the thumb is applied when the actuating rod is pushed forwardly to eject the chuck from the handle. As a result, the needle extraction operation and the chuck release operation can each be readily and rapidly carried out in respective optimum positions.

Because the rear surface portion of the actuating rod has a concave shape from a side view thereof, such that it readily fits the inner surface of the thumb, the thumb is prevented from slipping vertically on this surface. Further, this rear surface of the actuating rod can be provided with upper and lower parallel notches to provide further insurance against thumb slippage and thus to facilitate the chuck release operation.

The handle can be made of a light-weight synthetic resin, thus providing easy handling and construction.

A container for a chuck as described above is also provided according to the present invention. The container has a housing with an open area in which the chuck can be at least partially disposed, and a cover disposed over the housing open area for sealing the open area. The container also has a support member disposed in the housing open area for releasably receiving the chuck such that the insert portion of the chuck projects out of the support member, whereby when the cover is removed from the housing, the chuck can be attached to the handle without direct handling of the chuck. The support member can have a groove for releasably receiving the chuck. The support member can be fixed to the inner wall of the housing open area, and moreover, can be formed to be integral with the inner wall of the housing open area. The cover is adapted to hermetically seal the housing open area. The cover can have an open area in which the chuck can be at least partially disposed.

A container according to the present invention uses a minimum number of components, i.e., a housing, a cover, and a support member. The container can be equally easily used by both right-handed and left-handed persons. For a right handed person, the housing is grasped with the left hand and cover is removed with the right hand; then the chuck can be rapidly inserted into the handle which is grasped with the right hand.

It should be noted that, with respect to such a container, the chuck is received within the support member with the insert portion projecting out of the support member. Thus, a new chuck, which is to replace a used one, can be removed from the support member and attached to the handle without being touched by the operator. This is obviously preferable from a sanitary point-of-view. As is noted above, the container can be hermetically closed to prevent contamination and enable ready storage.

In operation, to extract a needle, the finger-holding surface of the handle is firmly grasped with the forefinger, middle finger, ring finger and little finger. Then the penetration position of the chuck is rapidly penetrated between the underside of the needle and the skin of the patient. Next the thumb is applied to the fingerholding surface of the actuating rod to push this surface down toward the handle while the actuating rod is grasped more tightly. As a result of pivoting the actuating rod with respect to the handle, the actuated piece, which in turn has been caused to pivot by the actuating rod, deforms the top portion of the needle laid across the needle-holding surfaces of the penetration portion of the chuck in the shape of a V. Then both claws of the needle are pulled from the patient's skin. In this manner, the needle is reliably and quickly extracted, thus reducing the pain for the patient.

BRIEF DESCRIPTION OF THE DRAWINGS

The above and other objects, features, and advantages of the present invention will be more fully apparent to those of ordinary skill in the art to which this invention pertains from the following detailed description when considered in connection with the accompanying drawings, in which like reference characters designate like or corresponding parts throughout the several views and wherein:

FIG. 9 is an enlarged perspective view illustrating a second embodiment of the insert portion of the chuck;

FIG. 10 is a partial side view illustrating a second embodiment of the finger-holding surface of the handle;

FIGS. 11-14 are sectional views illustrating the sequential steps for extracting a surgical needle from the skin of a a patient;

DETAILED DESCRIPTION OF THE INVENTION

Figure 1:
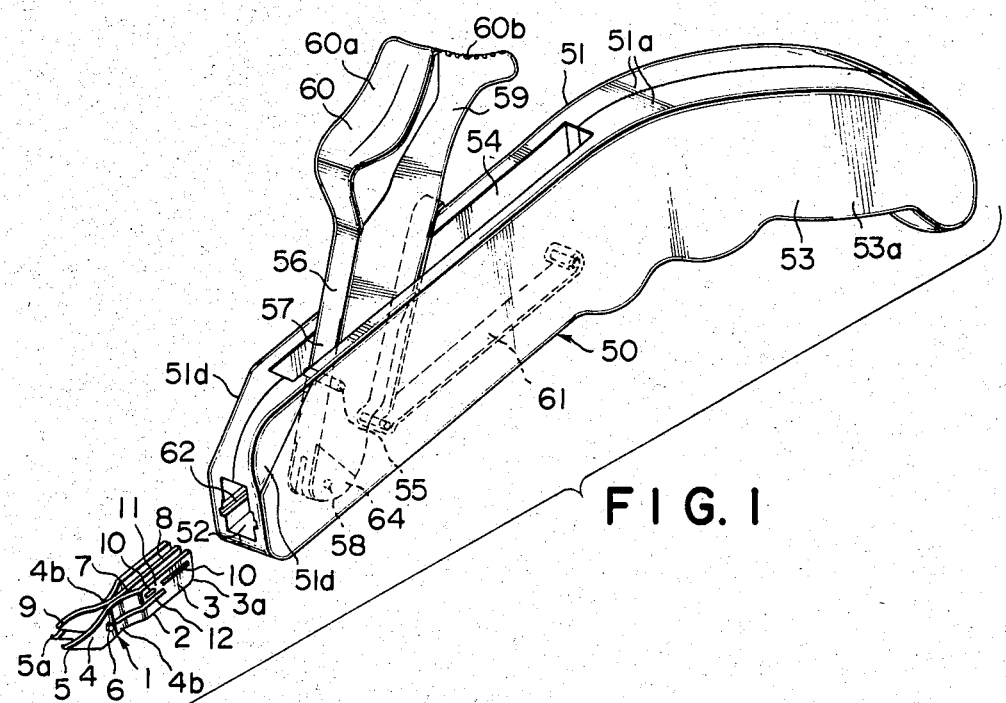
FIG. 1 is a perspective view illustrating a first embodiment of a surgical needle extractor according to the present convention, showing the chuck separated from the handle.
Figure 2:
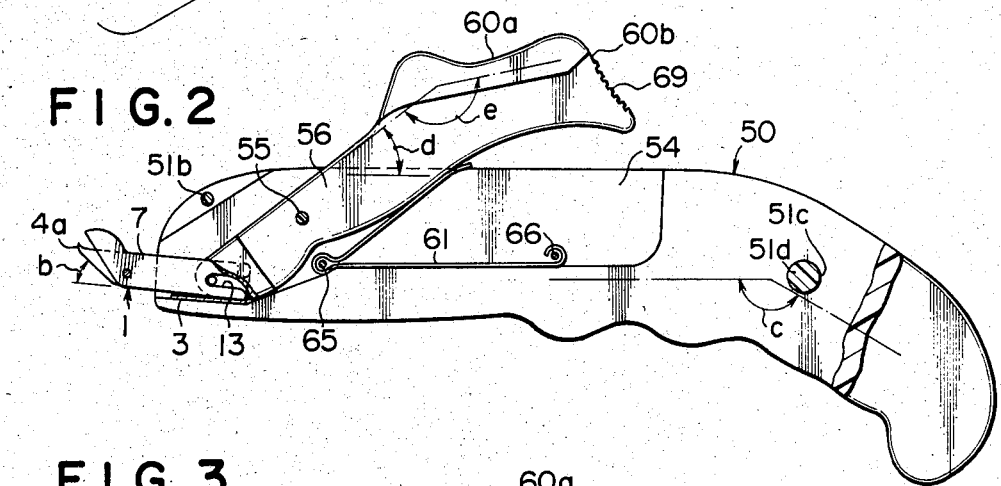
FIG. 2 is a partially-cutaway sectional, side view of the embodiment shown in FIG. 1.
Figure 3:
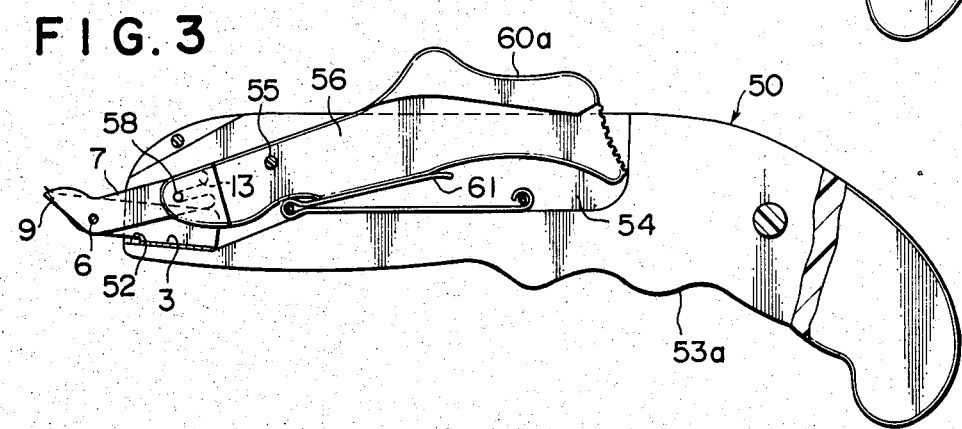
FIG. 3 is a vertical, sectional side view of the embodiment shown in FIG. 2 showing the actuating rod after having been pushed down.

FIGS. 1-5 illustrates a detachable-type surgical needle extractor, and FIGS. 6-9 illustrate a detachable-type surgical needle extractor having means for releasing the chuck from the handle.

FIGS. 1-5 show an extractor having a chuck 1 and a handle 50 for chuck 1. Chuck 1 has insert portion 3, body portion 2 which is made of a metal such as stainless steel and actuated piece 7 which is also made of a metal such as stainless steel. Insert portion 3 has a substantially U-shaped section from a front side view thereof. Insert portion 3 is for releasable attachment in a first recess 52 formed at the front end of handle portion 51 of handle 50. Insert portion 3 is detachably fitted to be releasably attached within first recess 52 without play. Body portion 2 of chuck 1 is formed as a unitary structure by a pair of first and second members 4 which extend from both sides of insert portion 3. As seen in the Figures, first and second members 4 are formed integrally with insert portion 3. That is, in the Figures, insert portion 3 is shown formed as members which are extensions of the first and second members 4. The front ends of first and second members 4 of chuck 1 are formed as penetration portions 5, which are preferably spaced apart a distance smaller than that between claws S1, as shown in FIGS. 11 and 12, of a conventional surgical needle S. Upper surfaces 5a of penetration portions 5 serve as needle-holding surfaces. Inclined undersurfaces 4a of first and second members 4 are contiguous with the undersurfaces of penetration portions 5 and function as surfaces which are brought into contact with the skin of a patient during extraction of a needle. Actuated piece 7 is pivotably attached between first and second members 4 at shaft 6. Actuated piece 7 has needle pushing portion 9 at its front end; when actuated piece 7 is pivoted about pivot shaft 6, needle pushing portion 9 is pivoted such that it is inserted between the two parts, as shown in the Figures, of penetration portion 5, and simultaneously, rear portion 8 of actuated piece 7 is pivoted away from insert portion 3 of chuck 1. Chuck 1 can be releasably attached within first recess 52 of handle 50.

Insert portion 3 of body portion 2 is beveled at the rear end of its underside to form inclined surface portion 3a to facilitate insertion of insert portion 3 into first recess 52. Projections 10 are provided on both sidewall surfaces of insert portion 3; projections 10 can be formed on either the upper or lower wall surfaces. Projections 10 make sliding engagement with grooves 62 formed in first recess 52 so that insert portion 3 is fitted within first recess 52 without play. Projections 10 extend longitudinally over the sidewalls of insert portion 3 like belts and are dimensioned such that they can slide within grooves 62 without vertical play. Projections 10 have indentations 11 at their midpoint; indentations 11 abut against projections 63, shown in FIG. 4, which are formed at the midpoint of grooves 62 in first recess 52. Indentations 11 abut against projections 63 after chuck 1 has been inserted into first recess 52. Projections 10 can be disposed on the upper parts of the sidewalls of insert portion 3 such that insert portion 3 can bend inwardly a sufficient amount to allow projections 10 to move over projections 63.

Longitudinal elongated holes 12 are formed in the middle part of body portion 2 including the rear half of first and second members 4 and the rear half of insert portion 3. This enables the elements forming chuck 1 to bend to a considerable extent so that the penetrating elements forming penetration portion 5 can be further expanded.

The portions of first and second members 4 of body portion 2 which are behind pivot shaft 6 and near insert portion 3 are constricted such that they form guide portion 4b. The distance between guide portions 4b is slightly larger than the thickness of actuated piece 7 such that actuated piece 7 can pivot between guide portions 4b without any side play.

Groove 13 is provided in the rear end of rear side 8 of actuated piece 7 which is releasably attached to handle 50. When chuck 1 is inserted into first recess 52, coupling portion 58 of actuating rod 56 fits in groove 13 with play. The inlet edge of groove 13 is beveled to facilitate insertion of coupling portion 58.

Alternatively, a penetration guiding collar 5b, shown in FIG. 9, connects the front ends of penetration portions 5 such that the pivoting motion of needle pushing portion 9 of actuated piece 7 between penetration portions 5 is not hindered.

The front end of handle 50 includes handle portion 51, which is preferably made of a synthetic resin material, actuating rod 56, which is also preferably made of a synthetic resin material, and spring 61. First recess 52 is formed at the front end of handle portion 51, insert portion 3 of chuck 1 is inserted in first recess 52, as described above. Rear side 53 of handle portion 51 functions as a finger holding surface 53a. Actuating rod 56 is pivotally attached at pivot shaft 55 located near first recess 52; front end 57 of actuating rod 56 is positioned in second recess 54 in handle 50. Second recess 54 is in communication with first recess 52 of handle 50. Coupling portion 58 of actuating rod 56 is formed at the front end of front side 57 of actuating rod 56; coupling portion 58 is releasably attached to the rear end of the rear side of actuated piece 7. Rear side 59 of actuating rod 56 is formed with a single holding portion 60.

Spring 61 is also attached in second recess 54 and functions to bias rear side 59 of actuating rod 56 such that coupling portion 58 of actuating rod 56 is in position within first recess 52 for attachment to the corresponding part of actuated piece 7, i.e., with groove 13 which, as describe above, is provided at the rear end of rear side 8 of actuated piece 7. Thus, chuck 1 can be releasably attached within first recess 52.

Handle 51 is formed as a unitary structure including a pair of right and left handle components 51a. One handle component 51a has a coupling shaft 51b and the other handle component 51a has a hole 51c in which coupling shaft 51b is engaged. That is, coupling shaft 51b is engaged in hole 51c to form the unitary handle assembly. Preferably finger-holding surface 53a of handle 51 is shaped to fit the inner surfaces of a forefinger, middle finger, ring finger and little finger. At the front end of the front side of handle 51, the right and left edges of the upper surfaces of handle 51 are beveled to form cut surfaces 51d. Therefore, the front end of the front side of handle 51 does not screen chuck 1 and thus does not hinder the vision of the operator.

Figure 4:
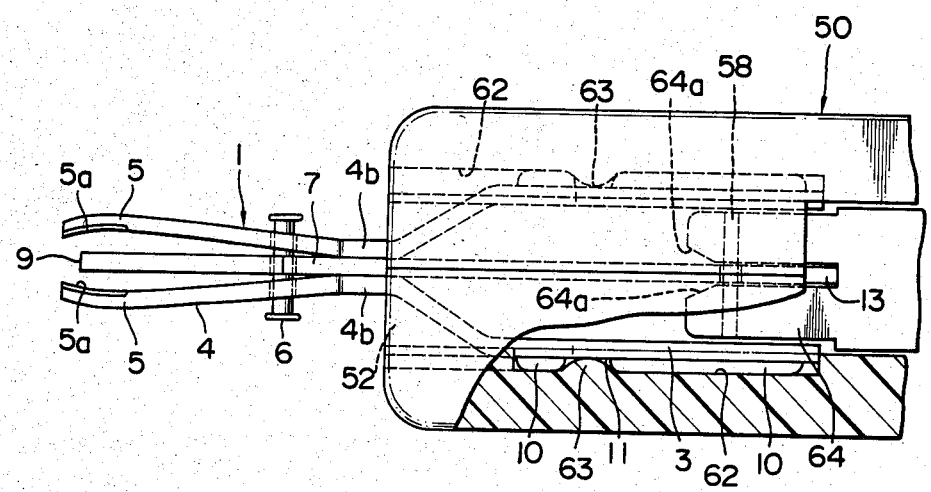
FIG. 4 is an enlarged plan view of a portion of the embodiment shown in FIG. 3.
Figure 5:
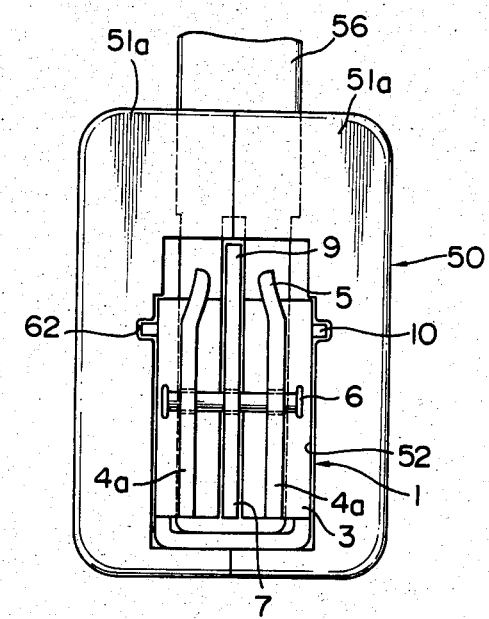
FIG. 5 is an enlarged front view of a portion of the embodiment shown in FIG. 4.

The inner wall surfaces of first recess 52 of handle 51 have grooves 62 which extend longitudinally from the inlet end toward the closed end of recess 52. Grooves 62 function to receive and guide projections 10 of insert portion 3 and to hold insert portion 3 within first recess 52 without play. Of course, insert portion 3 can be pulled out of first recess 52 along grooves 62. Grooves 62 have projections 63 at their midpoint, as shown in FIG. 4. Midpoint projections 63 engage with midpoint indentations 11 formed in insert portion 3 which is tightly fitted within first recess 52. Thus, chuck 1 will not come out of first recess 52 unless external force is applied thereto.

Front end portion 64 of front side 57 of actuating rod 56 is dimensioned to fit within insert portion 3 of chuck 1 with play. Front end portion 64 is also forked such that it clamps between its forked front edges or prongs 101 the rear end portion of rear side 8 of actuated piece 7. Coupling portion 58 of actuating rod 56 can be a pivot pin which engages groove 13 of actuated piece 7. Coupling portion or pivot pin 58 forms a bridge between prongs 101 of forked front end portion 54. Because coupling portion 58 is fitted in groove 13 with play, actuated piece 7 can freely pivot. Inner surfaces 64a of forked front edges or prongs 101 of front end portion 64 are beveled to facilitate attachment of actuated piece 7 to actuating rod 56.

The width of finger-holding surface 60 of actuating rod 56 is increased in upper surface portion 68a. Finger-holding surface 60 has a concave shape from a side-view thereof and a middle part of surface 60 also has a concave shape from a front side view thereof, such that surface 60 fits the inner surface of the thumb. As a result, the thumb does not slip either right or left nor up or down on surface 60.

One end of spring 61 is secured to shafts 65 and 66 mounted in second recess 54 and the other end of spring 61 abuts against the under surface of rear side 59 of actuating rod 56. Spring 61 biases actuating rod 56 such that the under surface of the front end portion 64 of actuating rod 56 is pushed against the floor of first recess 52 and such that coupling portion 58 is aligned with the sliding track of groove 13 of actuated piece 7 and is ready for attachment with the latter.

It should be noted that shafts 65 and 66 for securing springs 61, together with coupling shaft 51b and pivot shaft 55, are preferably formed with handle components 51a as an integral structure using a single metal mold.

Figure 6:
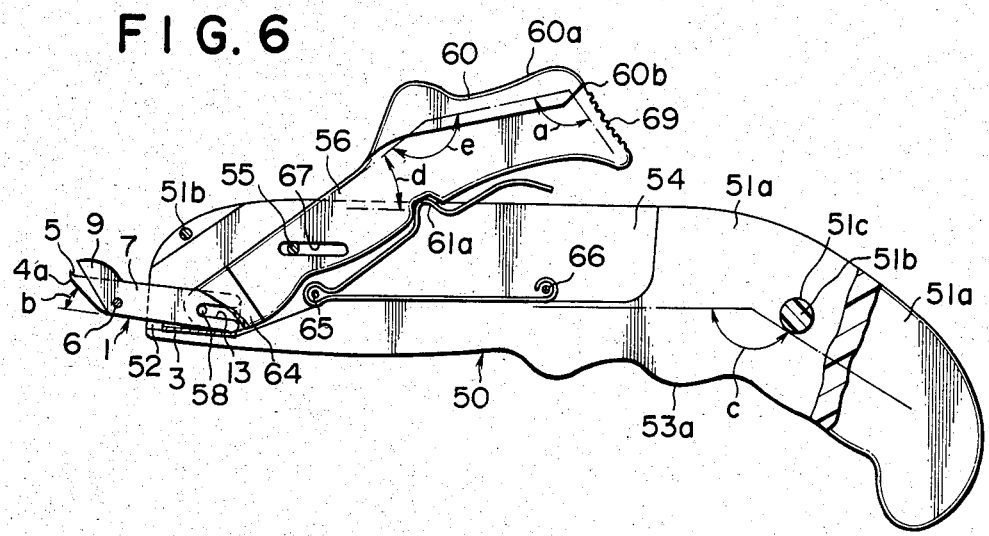
FIG. 6 is a partially-cutaway, vertical, sectional side view illustrating a second embodiment of the present invention.
Figure 7:
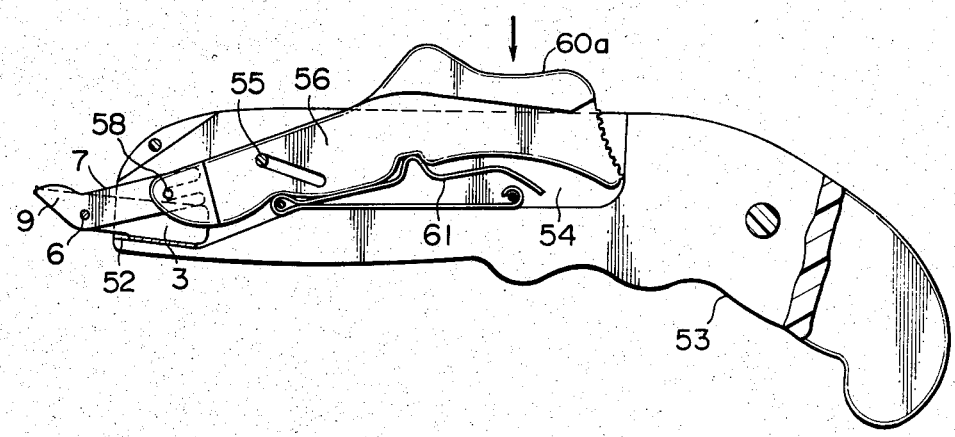
FIG. 7 is a vertical, sectional side view of the embodiment shown in FIG. 6, with the actuating rod shown after having been pushed down.
Figure 8:
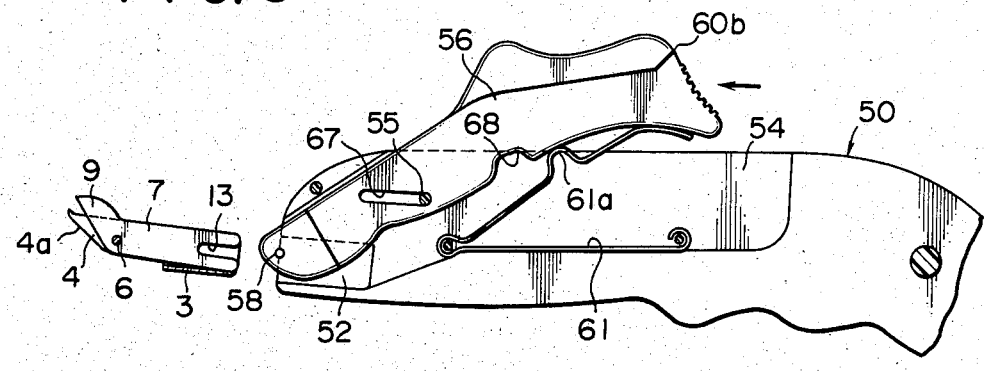
FIG. 8 is a vertical, sectional side view of the embodiment shown in FIG. 7, showing the actuating rod having been pushed forward to release the chuck from the handle.
Figure 13:
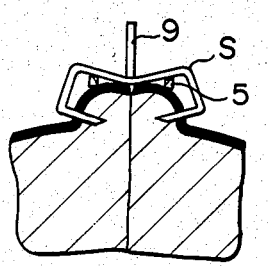
Figure 14:
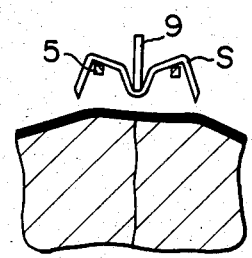

The handle for a surgical needle extractor shown in FIGS. 6–8 is identical in basic structure with the handle of the detachable-type surgical needle extractor shown in FIGS. 1–5, except that in FIGS. 6–8 means are provided for releasing chuck 1 from handle 51. As shown in FIGS. 1–5, chuck 1 can be pushed out of first recess 52 by means of actuating rod 56. In particular, longitudinal elongated hole 67 is provided in actuating rod 56 in which pivot shaft 55 is engaged. Thus, actuating rod 56 can slide with respect to pivot shaft 55 along longitudinal hole 67. In addition, coupling portion 58 on front side 57 of actuating rod 56 can be freely advanced, due to the sliding motion of actuating rod 56, until coupling portion 58 projects out of first recess 52; similarly, coupling portion 58 can be retracted within first recess 52. The under surface of rear side 59 of actuating rod 56 against which spring 61 abuts, is provided with indentation 68. Angled projection 61a of spring 61 abuts against and is engaged with indentation 68, except when chuck 1 is being pushed out of holder 51 by actuating rod 56. When projection 61a engaged with indentation 68, actuating rod 56 can swing about pivot axis 55 together with actuated piece 7 of chuck 1, which, of course, is within first recess 52, in an integrally cooperating manner. Indentation 68 can be moved beyond angled projection 61a and actuating rod 56 itself can move in the longitudinal direction within longitudinal, elongated hole 67, such that coupling portion 58 pushes actuated piece 7, as well as all of chuck 1, out of first recess 52. Finger-holding surface 60 of actuating rod 56 has rear surface portion 60b which is continuously inclined in a rearward direction below the rear side of upper surface portion 60a. The angle a of inclination, shown in FIG. 6, of rear surface portion 69b relative to upper surface portion 60a, is preferably approximately 60 degrees. Rear surface portion 60b has a concave shape from a side-view thereof so as to readily fit the entire inner surface of the thumb. Furthermore, upper and lower parallel projections 69 are provided to prevent the thumb from slipping vertically.

In each embodiment of the chuck and handle according to the present invention as illustrated in the Figures, angle b of skin-contacting surfaces 4a of chuck 1 is preferably approximately 40 degrees. The angle of bend c of finger-holding surface 53a of handle 50 is preferably approximately 150 degrees. The angle d of inclination of actuating rod 56 in its rest position relative to the front side of handle portion 51 is preferably approximately 40 degrees. The angle e formed by front side 57 and finger-holding surface 60 of actuating rod 56 is preferably approximately 155 degrees. Of course, these angles are not limited to the values indicated above, and any other values may be used unless handling is obstructed thereby.

Finger-holding surface 53a of handle portion 50 may be annular as shown in FIG. 10. In this case, handle portion 50 can be more readily handled because the forefinger, middle finger, ring finger and little finger can be inserted into the annular portion to hold the handle. Finger-holding surface 60 may also be made annular such that the thumb can be inserted into this annular portion.

In operation, with respect to a surgical needle extractor according to the present invention, finger-holding surface 53a of holder 51 is grasped by all four fingers and the thumb is applied to finger-holding surface 60 of actuating rod 56. Then, penetration portions 5 are inserted between the underside of needle S and the patient's skin. Actuating rod 56 is pushed down by the thumb to bend and extract needle S as illustrated in FIGS. 11-14.

After extraction, chuck 1 can be pulled out of first recess 52 by hand or by using any suitable tool. It may be pushed out by means of actuating rod 56 in the embodiment shown in FIGS. 6-8. When another surgical needle is to be extracted, a new chuck 1 is tightly fitted into first recess 52 of handle 51 and the needle can be removed in a similar manner for disposal.

Figure 15:
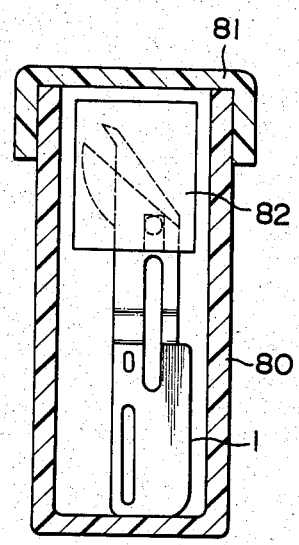
FIG. 15 is an enlarged, vertical sectional view illustrating a container for an exchangeable chuck according to the present invention.
Figure 16:
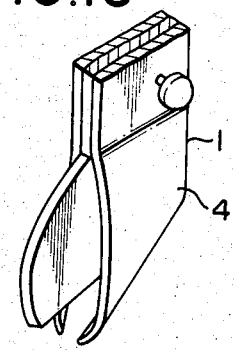
FIG. 16 is a partially-enlarged perspective view showing the chuck separated from the support member of the container.

FIG. 15 shows container 103 for a replaceable chuck 1. When chuck 1 is to be used, cover 81, which seals housing 80 of container 103, is removed and support member 82 of housing 80 is taken out. Chuck 1 can be separated from support member 82 and attached to handle 51 without direct handling, i.e., without chuck 1 itself ever being touched by the operator. Support member 82 has a mounting groove 83, as shown in FIG. 16, in which chuck 1 is disposed up to a position corresponding to pivot shaft 6 of first and second members 4. Thus, chuck 1 is fitted within support member 82 except for insert portion 3 which projects out of support member 82.

Cover 81 preferably hermetically seals the open area within housing 80.

FIG. 16 shows chuck 1 and support member 82 with groove 83 formed in support member 82.

Figure 17:
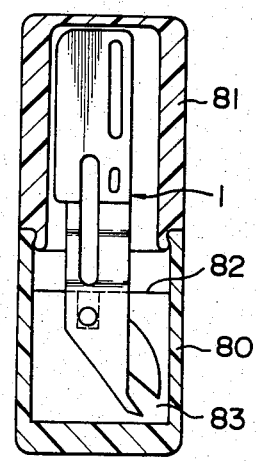
FIG. 17 is an enlarged, vertical sectional view showing a second embodiment of the chuck according to the present invention.
Figure 18:
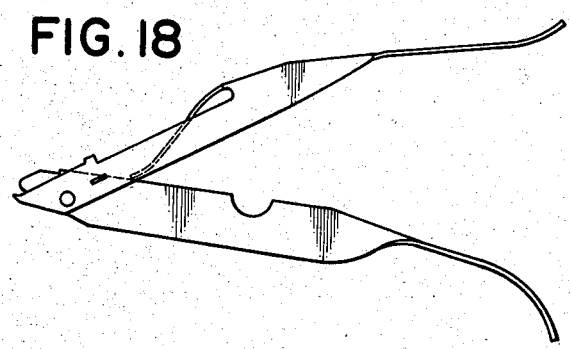
FIG. 18 is a side view of a conventional surgical needle extractor.

FIG. 17 illustrates chuck container 103 which is made of 2 components, i.e., housing 80 and cover 81. In this embodiment, support 82 is integrally formed on the inner bottom surface of housing 80. Further, cover 81 includes an open area in which the chuck is partially disposed.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A surgical needle extractor comprising:
   (a) a chuck including a penetration portion comprising means for penetrating between the claws of a surgical needle, and an actuated piece pivotable on said penetration portion; and
   (b) a handle to which said chuck is releasably attached, said handle including a body and pivoting means for pivoting said actuated piece with respect to said penetration portion, wherein said body includes a first recess therein, wherein said penetration portion and said actuated piece are releasably attached to said body only in said first recess, wherein said pivoting means comprises an actuating rod pivoted on said body and extending through said recess to pivot said actuated piece such that when said penetration portion is inserted between said claws, said penetration portion and said actuated piece cooperate to remove said needle.

2. The apparatus as recited in claim 1 wherein said actuating rod is releasably attached to said actuated piece, said actuating rod being adapted to be hand-operated wherein said chuck includes an insert portion and said body further includes a second recess, wherein said first and second recesses are in communication with each other, said insert portion of said chuck being releasably attached within said first recess, one end of said actuated piece being disposed in said first recess, said actuating rod being pivotally attached to a pivot axis in said second recess, one end of said actuating rod being releasably attached to said end of said actuated piece disposed in said first recess and the other end of said actuating rod extending out of said second recess, wherein said insert portion has a substantially U-shaped section, wherein said chuck is an integral structure comprising said first and second members, said first and second members and said actuated piece forming an integral structure, wherein the upper surface of each penetration portion is adapted as a needle holding surface and the undersurface of each penetration portion is adapted as a surface for contacting the skin of a patient, said actuated piece being adapted at one end to push a needle and said penetration portions being connected to each other by a penetration guiding collar, wherein said first recess includes at least two grooves formed in opposite walls thereof and wherein said insert portion includes a corresponding number of projections for engagement with said grooves, said insert portion projections being longitudinal with respect to said insert portion.

3. The apparatus as recited in claim 1 further comprising biasing means for biasing said actuating rod such that such actuating rod is in position for attachment to said actuated piece when said insert portion and said actuated piece are inserted into said first recess, said biasing means comprising a spring disposed within said second recess.

4. The apparatus as recited in claim 1 wherein said chuck further includes first and second members, one end of each of said first and second members comprising a penetration portion for penetration between the claws of a surgical needle, said actuated piece being disposed between and pivotably attached to said first and second members, the other ends of said first and second members being releasably attached to said handle, said pivoting means including means for pivoting said actuated piece with respect to said first and second members, said pivoting means including an actuating rod pivotably attached to said handle and releasably attached to said actuated piece, said actuating rod being adapted to be hand operated, wherein said apparatus further comprises means for releasing said chuck from said handle, wherein said first and second members form a constricted guide portion for guiding said actuated piece such that the pivoting motion of said actuated piece is not hindered, wherein said first and second members each include elongated holes, wherein said chuck is formed of metal, and wherein said handle includes a finger holding surface.

5. The extractor as recited in claim 1 wherein said actuating rod further comprises a front end and a rear end, wherein said actuating rod is pivoted on said body at a pivot point intermediate said front and rear ends of said actuating rod.

6. The extractor as recited in claim 5 wherein said body further comprises spaced apart side walls, wherein said actuating rod is positioned between said side walls, wherein said body includes a second recess therein, through which said actuating rod extends, wherein said actuating rod comprises a front portion extending from said pivot point to said front end, wherein said front portion of said actuating rod extends through said first recess to pivot said actuated piece, wherein said front portion of said actuating rod is entirely positioned within said recess.

7. The extractor as recited in claim 6 wherein said body comprises front and rear ends, wherein said pivot point is positioned intermediate said front and rear ends of said body.

8. A surgical needle extractor comprising:
(a) a chuck including a penetration portion comprising means for penetrating between the claws of a surgical needle, and an actuated piece pivotable with respect to said penetration portion; and
(b) a handle to which said chuck is releasably attached, said handle including pivoting means for pivoting said actuated piece with respect to said penetration portion such that when said penetration portion is inserted between said claws, said penetration portion and said actuated piece cooperate to remove said needle, wherein said extractor further comprises means for releasing said chuck from said handle, wherein said pivoting means includes an actuating rod releasably attached to said actuated piece, and wherein said means for releasing includes said actuating rod, said actuating rod being slidably attached to said handle, whereby sliding said rod with respect to said handle releases said chuck from said handle, said actuating rod being adapted to be hand-operated.

9. A surgical needle extractor comprising:
(a) a chuck including a penetration portion comprising means for penetrating between the claws of a surgical needle, and an actuated piece pivotable with respect to said penetration portion; and
(b) a handle to which said chuck is releasably attached, said handle including pivoting means for pivoting said actuated piece with respect to said penetration portion such that when said penetration portion is inserted between said claws, said penetration portion and said actuated piece cooperate to remove said needle, wherein said pivoting means includes an actuating rod pivotably atatched to said handle and releasably attached to said actuated piece, wherein said chuck includes an insert portion and said handle includes first and second recesses in communication with each other, said insert portion of said chuck being releasably attached within said first recess, one end of said actuated piece being disposed in said first recess, said actuating rod being pivotably attached to a pivot axis in said second recess, one end of said actuating rod being releasably attached to said end of said actuated piece disposed in said first recess and the other end of said actuating rod extending out of said second recess, wherein said actuating rod includes a coupling portion at its end which is releasably attached to said actuated piece, said coupling portion including a pivot pin and said actuated piece including a groove for connection with said pivot pin.

10. A chuck for a surgical needle extractor, said needle extractor having a handle, wherein said chuck is adapted to be releasably attached to a first recess in the body of said handle, wherein said handle further comprises an actuating rod adapted to actuate said chuck, wherein said chuck comprises:
(a) first and second members attached to one another, one end of each of said first and second members comprising a penetration portion for penetrating between the claws of a surgical needle;
(b) an actuated piece disposed between and pivotally attached to said first and second members at a pivot point; and
(c) means for releasably attaching said penetration portion and said actuated piece only in said first recess of said body of said handle and for releasably attaching said actuated piece within said first recess to said actuating rod of said handle.

11. The apparatus as recited in claim 10 wherein said other ends of said first and second members comprise an insert portion comprising means for inserting in a recess formed in a handle.

12. The chuck as recited in claim 10 wherein said attaching means is positioned behind said pivot point.

13. The chuck as recited in claim 12 wherein said first recess is bounded by opposite walls, each having a longitudinal groove therein, wherein said first and second members each comprise an outer wall comprising a longitudinal projection thereon, adapted to be received in one of said grooves in said walls of said first recess, wherein each groove comprises at least one projections therein, wherein each projection of said chuck further comprises at least one indentation therein, adapted to engage one of said projections in said grooves, wherein said outer walls of said first and second members are spaced further apart than said projections on said grooves in said opposite walls bounding said said first recess, wherein said outer walls of said first and second members comprises bendable elements adapted to bend over said projections in said grooves as said chuck is inserted into said first recess so permit said chuck to be inserted into said first recess.

14. The chuck as recited in claim 13 wherein said first and second members have a longitudinal opening in said first and second members.

15. The handle as recited in claim 10 wherein said body further comprises spaced apart side walls, wherein said actuating rod is positioned between said side walls, wherein said body includes a second recess therein, through which said actuating rod extends, wherein said actuating rod comprises a front portion extending from said pivot point to the front end of said actuating rod, wherein said front portion of said actuating rod extends through said first recess to pivot said actuated piece, wherein said front portion of said actuating rod is entirely positioned within said recess.

16. The handle as recited in claim 15 wherein said body comprises front and rear ends, wherein said pivot point is positioned intermediate said front and rear ends of said body.

17. The chuck defined by claim 10 wherein said extractor comprises a handle, said chuck further comprising an insert portion having a substantially U-shaped section, said insert portion being releasably attachable within said first recess formed at the front end of said handle by said releasably attaching means, wherein said chuck further comprises a body portion being formed as a unitary structure by said first and second members, wherein said body extends from both sides of said insert portion, wherein said one end of said first and second members comprises a front end of said first and second members, wherein said front ends of said first and second members each comprise a penetration portion and are spaced apart a predetermined distance, wherein said penetration portions of said first and second members each comprise an inclined undersurface, wherein said first and second members further comprise an upper surface and an inclined undersurface, wherein said upper surface of said first and second members serve as needle holding surfaces, wherein said inclined undersurfaces of said first and second members adjacent to the said undersurface of said penetration portions serve as surfaces which are brought into contact with the skin of a patient, wherein said body portion further comprises a pivot shaft pivotally attaching said actuated piece to said first and second members at said pivot point, wherein said actuating piece has at its front end a needle pushing portion which is pivotable between said penetration portions, the rear side portion of said actuated piece being pivotable about said pivot shaft away from said insert portion.

18. The chuck as recited in claim 17 wherein said insert portion has a projection on its outer wall surfaces for engagement with a groove formed in a recess of a handle.

19. The chuck defined by claim 17, wherein said said insert portion further comprises a projection, wherein said projection is longitudinal, said projection having a midpoint indentation for engaging a midpoint projection formed in a groove in a recess of said handle, said actuated piece including a groove for releasable attachment to a coupling portion of an actuating handle rod, said first and second members being constricted to form a guide portion for holding said actuated piece, said body portion having longitudinal, elongated holes in middle portions of its side walls, said holes extending to the rear half of said first and second members and to the front half of said insert portion, said penetration portions being connected to each other by a penetration guiding collar, and said chuck being formed of metal.

20. A handle for a surgical needle extractor chuck, wherein said chuck comprises a penetration portion comprising means for penetrating between the claws of a surgical needle and an actuated piece pivotable on said penetration portion, said handle comprising:
(a) a body having a first recess therein;
(b) means for releasably attaching said chuck to said body; and
(c) pivoting means for pivoting said actuated piece with respect to said penetration portion, wherein said pivoting means is pivotally attached to said body at a pivot point and extends through said first recess such that when said penetration portion is inserted between said claws, said penetration portion and said actuated piece cooperate to remove said needle, wherein said means for releasably attaching said chuck to said handle further comprises means for releasably attaching said pivoting means to said actuated piece, and wherein said first recess comprises means for releasably holding said penetration portion and said actuated piece therein.

21. The handle as recited in claim 20, further comprising a second recess, wherein said first and second recesses are in communication with each other, said first recess comprising means for releasably attaching said chuck to said first recess, said actuating rod being pivotably attached to a pivot shaft in said second recess, one end of said actuating rod comprising means for releasably attaching said chuck to said actuating rod within said first recess, the other end of said actuating rod extending out of said second recess, said actuating rod being adapted to be hand-operated.

22. The handle as recited in claim 20 wherein said pivoting means comprises an actuating rod, wherein said actuating rod further comprises a front end and a rear end, wherein said actuating rod is pivoted on said body at a pivot point intermediate said front and rear ends of said actuating rod.

23. The handle as recited in claim 20 wherein said first recess is bounded by opposite walls, each having a longitudinal groove therein, wherein each groove comprises at least one projection therein, wherein said projection of one groove is positioned at substantially the same point along the length of said first recess as said projection of the other groove, wherein the distance between said projections is less than the width of said chuck.

24. A handle for a surgical needle extractor chuck, wherein said chuck comprises a penetration portion comprising means for penetrating between the claws of a surgical needle and an actuated piece pivotable with respect to said penetration portion, said handle comprising:
(a) means for releasably attaching said chuck to said handle; and
(b) pivoting means for pivoting said actuated piece with respect to said penetration portion such that when said penetration portion is inserted between said claws, said penetration portion and said actuated piece cooperate to remove said needle, wherein said handle further comprises first and second recesses in communication with each other, said first recess comprising means for releasably attaching said chuck to said first recess, said actuating rod being pivotably attached to a pivot shaft in said second recess, one end of said actuating rod comprising means for releasably attaching said chuck to said actuating rod within said first recess, the other end of said actuating rod extending out of said second recess, said actuating rod being adapted to be hand-operated, said handle further comprising biasing means for biasing said actuating rod such that said actuating rod is in position for attachment to said chuck when said chuck is inserted into said first recess, said biasing means comprising a spring disposed within said second recess, said releasing means including said actuating rod, said actuating rod being slidably attached to said pivot shaft, whereby sliding said rod with respect to said shaft releases said chuck from said handle, said actuating rod being slidably attached to said pivot shaft in an elongated hole formed in said actuating rod such that said actuating rod will slide with respect to said shaft along said elongated hole.

25. A surgical needle extractor comprising a chuck and a handle to which said chuck can be releasably attached, said chuck comprising an insert portion having a substantially U-shaped section, said insert portion being releasably attached within a first recess formed at the front end of said handle, said chuck being formed as a unitary structure by first and second members which extend from both sides of said insert portion, the front ends of said first and second members forming penetration portions spaced apart a predetermined distance, the upper surfaces of said penetration portions serving as needle holding surfaces, the inclined undersurfaces of said first and second members adjacent to said penetration portions serving as surfaces for contacting the skin of a patient, said chuck further comprising an actuated piece pivotably attached between said first and second members, said actuated piece having at its front end a needle pushing portion which can be pivoted between said penetration portions while the rear side portion of said actuated piece is pivoted away from said insert portion, said handle comprising a first recess at its front end, said first recess comprising means for receiving said insert portion of said chuck, the rear side portion of said handle serving as a finger-holding surface, said handle further comprising an actuating rod pivotably attached to said handle at a pivot shaft disposed near said first recess, the front side portion of said actuating rod being disposed in a second recess in said handle which is in communication with said first recess, the front end of the front side portion of said actuating rod having a coupling portion adapted for releasable attachment to the rear side portion of said actuated piece to allow pivoting motion of said actuating piece, the rear side portion of said actuating rod serving as a finger-holding surface, wherein said handle further comprises a spring disposed in said second recess wherein said spring comprises means for biasing said coupling portion of said actuating rod into said releasable attachment with said rear side portion of said actuated piece as said chuck is being inserted in said first recess.

26. The extractor as recited in claim 25 wherein said actuating rod is slidingly attached to said handle, whereby sliding said rod with respect to said handle releases said chuck from said handle.

27. A handle for use in a surgical needle extractor, said handle comprising a handle portion having a first recess disposed at the front end of said handle portion for detachably receiving an insert portion of a chuck without play, the rear side portion of said handle portion serving as a finger-holding surface, an actuating rod pivotably attached, to said handle portion at a pivot shaft disposed near said first recess, the front side portion of said actuating rod being disposed in a second recess in said handle portion which is in communication with said first recess of said handle portion, a coupling portion formed at the front end of the front side portion of said actuating rod for releasable attachment to the rear end of the rear side portion of an actuated piece of a chuck, the rear side portion of said actuating rod serving as a finger holding surface, wherein said handle further comprises a spring disposed in said second recess wherein said spring comprises means for biasing said coupling portion of said actuating rod into said releasable attachment with said rear side portion of an actuated piece of a chuck as said chuck is inserted in said first recess.

28. The handle as recited in claim 27 wherein said first recess includes a groove in its inner wall surface for engagement with a projection on a chuck.

29. The handle as recited in claim 28 wherein said groove includes a midpoint projection for engagement with a midpoint indentation formed in a chuck.

30. The handle as recited in claim 27 wherein said chuck comprises an actuated piece and a penetration portion, wherein said penetration portion comprises two spaced apart walls, wherein said actuated piece is positioned between said walls of said penetration portion, wherein the width of said first recess is substantially equal to the distance between said spaced apart walls of said penetration portion of said chuck, wherein said first recess comprises means for housing both said penetration portion and said actuated piece.

31. The handle as recited in claim 30 wherein said actuating rod comprises a front portion, wherein the entire front portion of said rod is positioned in said first recess.

32. A handle for use in a surgical needle extractor, said handle comprising a handle portion having a first recess disposed at the front end of said handle portion for detachably receiving an insert portion of a chuck without play, the rear side portion of said handle portion serving as a finger-holding surface, an actuating rod pivotably attached to said handle portion at a pivot shaft disposed near said first recess, the front side portion of said actuating rod being disposed in a second recess in said handle portion which is in communication with said first recess of said handle portion, a coupling portion formed at the front end of the front side portion of said actuating rod for releasable attachment to the rear end of the rear side portion of an actuated piece of a chuck, the rear side portion of said actuating rod serving as a finger holding surface, and a spring disposed in said second recess for biasing the rear side portion of said actuating rod such that said coupling portion of said actuating rod is in position for attachment with the rear end of the rear side portion of an actuated piece of a chuck, wherein said first recess includes a groove in its inner wall surface for engagement with a projection on a chuck, wherein said groove includes a midpoint projection for engagement with a midpoint indentation formed in a chuck, wherein said coupling portion includes a pivot pin for attachment in a groove in a chuck with play, said pivot pin connecting two portions of a forked front end of said actuating rod, said forked front end having a width such that it can be fitted into an insert portion of a chuck with play, said forked front end being adapted to hold the rear portion of an actuated piece of a chuck disposed in a groove in said actuated piece, the inner surfaces of the top ends of said forked front end being beveled, said finger-holding surface of said actuating rod having a concave shape such that it can fit the inner surface of a thumb.

33. The handle as recited in claim 32 wherein said finger holding surface has a concave shape from a side view and from a front view thereof, said finger holding surface being annular and the finger holding surface of said handle portion also being annular.

34. The handle as recited in claim 33 wherein said handle portion includes a pair of right and left handle components, a shaft being disposed on one said holder component for coupling said handle components to each other, said pivot shaft to which said actuating rod is attached and a shaft for securing said spring in said second recess being disposed in respective corresponding holes provided in the other said handle component such that a unitary handle is formed.

35. The handle as recited in claim 34 wherein said actuating rod includes a longitudinal elongated hole through which a pivot shaft is disposed to pivotably and slidably attach said actuating rod to said handle portion, said spring including an angled projection for engagement with an indentation formed in the rear side portion of said actuating rod, said actuating rod being pivotable about said pivot shaft and guided thereby such that said actuating rod can be advanced until said coupling portion projects from within said first recess, said finger holding surface of said actuating rod having a rear surface portion continuously inclined rearwardly from the rear end of the upper surface of said actuating rod, said rear surface portion of said actuating rod having a concave shape, the angle of bend of the rear side portion of said handle portion with respect to the front side portion of said handle portion being approximately 150°, the angle of inclination of said actuating rod with respect to the front side portion of said handle portion being approximately 40°, the angle formed by the front side portion and the finger-holding surface of said actuating rod being approximately 155°, and the angle of inclination of the rear surface portion of said finger-holding surface of said handle portion relative to the upper surface of said handle portion being approximately 60°, each component of the handle being formed from a synthetic resin material, with the exception of said spring.

* * * * *

UNITED STATES PATENT AND TRADEMARK OFFICE
CERTIFICATE OF CORRECTION

PATENT NO. : 4,640,274

DATED : February 3, 1987

INVENTOR(S) : T. NAKAMOTO

It is certified that error appears in the above-identified patent and that said Letters Patent is hereby corrected as shown below:

At column 8, line 3, "a" (second occurrence) is deleted;
At column 14, line 24, "atached" should read ---attached---; and
At column 16, line 3, "said" (second occurrence) is deleted.

Signed and Sealed this

Second Day of February, 1988

Attest:

DONALD J. QUIGG

Attesting Officer

Commissioner of Patents and Trademarks